United States Patent
Wagner et al.

(10) Patent No.: US 6,824,530 B2
(45) Date of Patent: Nov. 30, 2004

(54) COMBINATION NEEDLE ASSEMBLY AND NEEDLE SAFETY GUARD

(75) Inventors: James E. Wagner, Cheektowaga, NY (US); Carmen V. Gaines, Buffalo, NY (US); Donald Nitsche, Alden, NY (US); Robert P. Michaloski, Hamburg, NY (US)

(73) Assignee: Harmac Medical Products, Inc., NY (US)

( * ) Notice: Subject to any disclaimer, the term of this patent is extended or adjusted under 35 U.S.C. 154(b) by 137 days.

(21) Appl. No.: 10/124,927

(22) Filed: Apr. 18, 2002

(65) Prior Publication Data

US 2002/0173749 A1 Nov. 21, 2002

Related U.S. Application Data

(60) Provisional application No. 60/290,329, filed on May 11, 2001.

(51) Int. Cl.$^7$ ................................. A61M 5/32
(52) U.S. Cl. ................. 604/162; 604/110; 604/263; 128/919
(58) Field of Search ................. 604/162, 177, 604/110, 263, 171, 198, 192, 165.03; 128/919

(56) References Cited

U.S. PATENT DOCUMENTS

| | | |
|---|---|---|
| 3,310,051 A | 3/1967 | Schulte |
| 4,627,843 A | 12/1986 | Raines |
| 4,631,058 A | 12/1986 | Raines |
| 4,733,661 A | 3/1988 | Palestrant |
| 5,167,629 A | 12/1992 | Vertenstein et al. |
| 5,192,275 A | 3/1993 | Burns |
| 5,279,588 A | 1/1994 | Nicoletti et al. |
| 5,290,255 A | 3/1994 | Vallelunga et al. |
| 5,295,972 A * | 3/1994 | Mischenko ............... 604/192 |
| 5,330,438 A | 7/1994 | Gollobin et al. |
| 5,352,204 A | 10/1994 | Ensminger |
| 5,460,612 A | 10/1995 | Madore |
| 4,476,452 A | 12/1995 | Thompson |
| 5,476,452 A | 12/1995 | Thompson |
| 5,571,092 A | 11/1996 | Thompson |
| 5,613,945 A | 3/1997 | Cai et al. |
| 5,690,645 A | 11/1997 | Van Erp |
| 5,695,470 A | 12/1997 | Roussigne et al. |
| 5,755,694 A | 5/1998 | Camus |
| 5,879,330 A | 3/1999 | Bell |
| 5,921,969 A | 7/1999 | Vallelunga et al. |
| 5,951,522 A | 9/1999 | Rosato et al. |
| 5,997,504 A | 12/1999 | Bell |
| 6,074,364 A | 6/2000 | Paul |
| 6,171,284 B1 * | 1/2001 | Kao et al. ............... 604/192 |
| 6,267,750 B1 * | 7/2001 | Utterberg ............... 604/264 |
| 6,280,420 B1 * | 8/2001 | Ferguson et al. ............... 604/198 |
| 6,409,706 B1 * | 6/2002 | Loy ............... 604/198 |
| 6,537,259 B1 * | 3/2003 | Niermann ............... 604/263 |
| 6,629,959 B2 * | 10/2003 | Kuracina et al. ............... 604/192 |
| 2002/0072716 A1 * | 6/2002 | Barrus et al. ............... 604/192 |

FOREIGN PATENT DOCUMENTS

| | | |
|---|---|---|
| EP | 0 410 734 A1 | 1/1991 |
| EP | 0 558 162 A2 | 9/1993 |
| EP | 0 629 277 A2 | 1/1996 |
| FR | 2725902 | 4/1996 |
| FR | 2 725 902 | 4/1996 |
| GB | 2259254 | 3/1993 |
| GB | 2 259 254 A | 3/1993 |
| WO | 93/01851 | 2/1993 |
| WO | 93/16745 | 9/1993 |
| WO | WO 00/50109 | 8/2000 |

* cited by examiner

*Primary Examiner*—Brian L. Casler
*Assistant Examiner*—Cris L. Rodriguez
(74) *Attorney, Agent, or Firm*—Piper Rudnick LLP

(57) ABSTRACT

A safety guard adapted for use with a Huber needle assembly that includes a main body, a pair of butterfly wings extending outwardly from the main body and a needle.

1 Claim, 4 Drawing Sheets

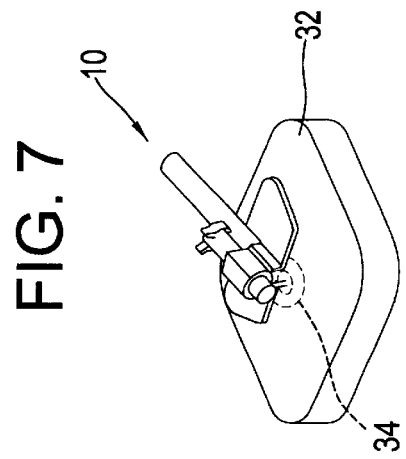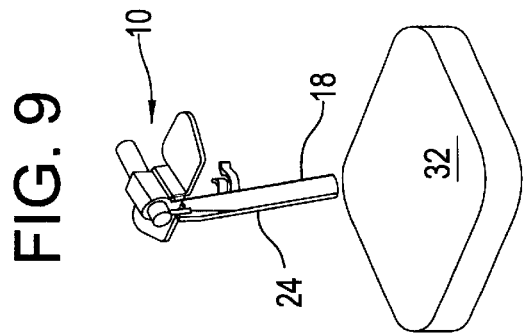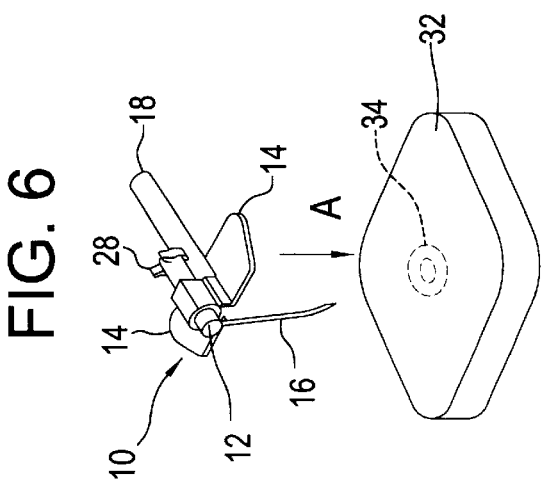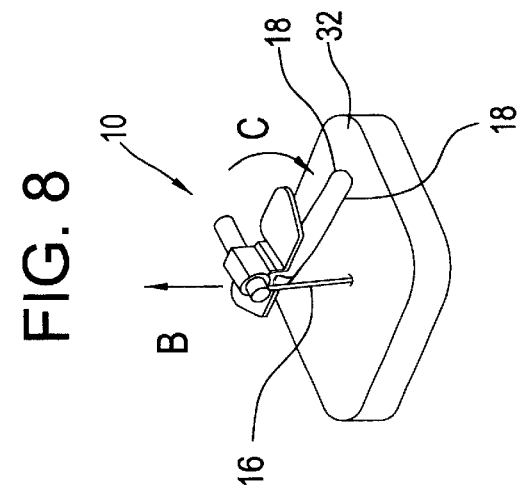

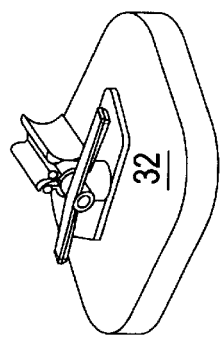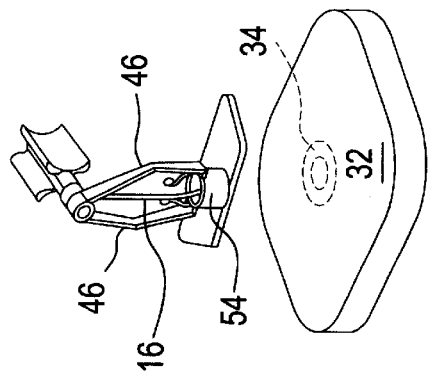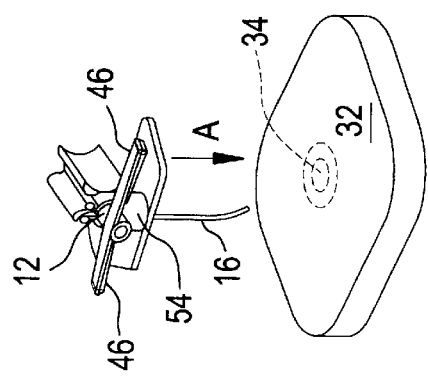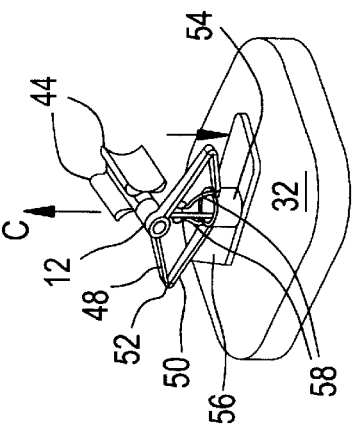

COMBINATION NEEDLE ASSEMBLY AND NEEDLE SAFETY GUARD

This application claims the benefit of priority to U.S. provisional patent application Ser. No. 60/290,329 filed on May 11, 2001.

FIELD OF THE INVENTION

This invention relates to a needle safety guard, particularly to an needle safety guard applicable to and intended for use in conjunction with a needle assembly, especially a Huber needle assembly.

BACKGROUND

Huber needles are widely used in the medical field, typically in oncology applications in conjunction with vascular access devices, particularly those located subcutaneously. As with other applications of needles utilized in conjunction with vascular applications, it is specially important to cover or shield used needles from the patient, other patients or healthcare providers. In that regard, it is important to provide protective measures that are not only effective, but that are easy to use and relatively low in cost.

SUMMARY OF THE INVENTION

In one aspect, the invention relates to a safety guard adapted for use with a needle assembly that includes a main body, a pair of butterfly wings extending outwardly from the main body and a needle extending at an angle, preferably perpendicularly, from an end portion of the main body comprising: an elongated substantially hollow shield, the shield having open ends and an elongated slot extending between the open ends; a spring connected to the assembly and the shield such that the slot and the needle are substantially parallel; and a fastener adapted to position the shield in a first position substantially parallel to the main body, and to permit the shield to pivot to a second position through spring force to surround and/or trap the needle.

In another aspect, the invention relates to a safety guard adapted for use with a needle assembly that includes a main body, a pair of butterfly wings extending outwardly from the main body and a needle extending at an angle, preferably perpendicularly, from an end portion of the main body comprising: a shield having opposed open ends; a coiled spring surrounding the needle and connected between the main body end portion and the shield; and a fastener adapted to position the shield in a first position relative to the butterfly wings such that the shield does not impede contact of the butterfly wings with a patient target surface, and to permit the shield to slide to a second position through spring force to surround and/or trap a distal end portion of the needle.

In yet another aspect, the invention relates to a combination needle assembly and needle safety guard comprising: a main body; a needle extending at an angle, preferably perpendicularly, from an end portion of the main body; a shield having opposed open ends and having a hollow portion slidably positioned around the needle; a pair of folding legs connected between the main body and the shield; and a fastener adapted to position the shield in a first position to maximize the needle exposure, and to permit the shield to slide along the needle to a second position through unfolding of the legs to surround and/or trap a distal end portion of the needle.

BRIEF DESCRIPTION OF THE DRAWINGS

FIG. 6 is a schematic perspective view of the embodiment of FIG. 1 shown in position just prior to insertion or application to a patient's skin surface.

FIG. 7 is a schematic perspective view of the embodiment shown in FIG. 1 already inserted into the patient's skin surface.

FIG. 8 is a schematic perspective view of the embodiment shown in FIG. 1 being removed from the patient's skin surface.

FIG. 9 is a schematic perspective view of the embodiment of FIG. 1 having been removed from the patient's skin surface.

FIG. 14 is similar to FIG. 6 except that a third embodiment of the apparatus of the invention is employed.

FIG. 15 is similar to FIG. 7 except that a third embodiment of the invention is utilized.

FIG. 16 is similar to FIG. 8 except that a third embodiment of the apparatus of the invention is employed.

FIG. 17 is similar to FIG. 9 except that a third embodiment of the invention is employed.

DETAILED DESCRIPTION

Figure 2:
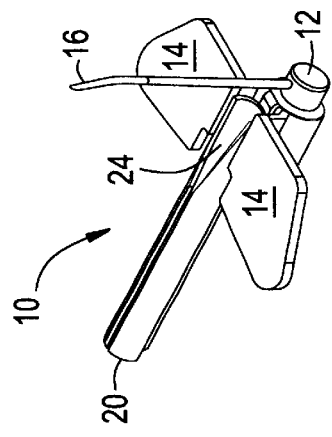
FIG. 2 is a bottom perspective view of the embodiment shown in FIG. 1.
Figure 5:
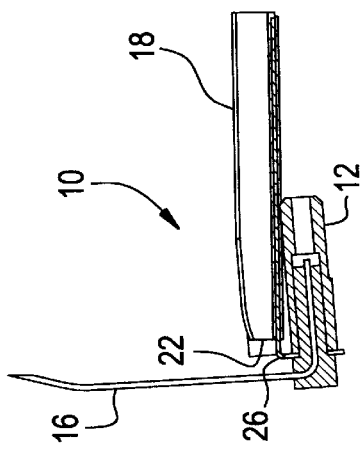
FIG. 5 is a cross section taken along the lines A-A in FIG. 4.
Figure 1:
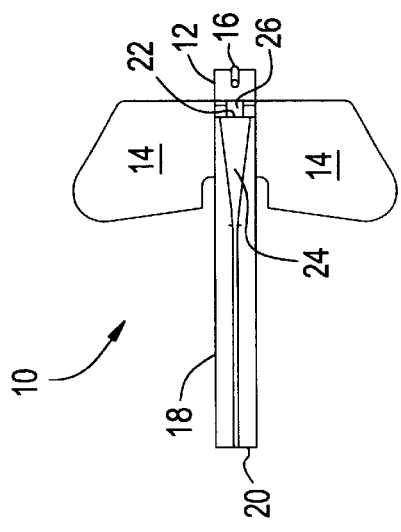
FIG. 1 is a bottom plan view of a first embodiment of a needle assembly and needle safety guard in accordance with aspects of the invention.
Figure 4:
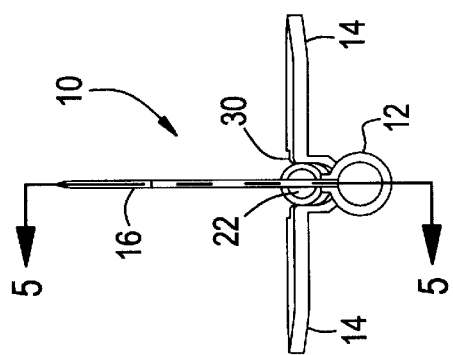
FIG. 4 is a front end view of the embodiment shown in FIG. 1.
Figure 3:
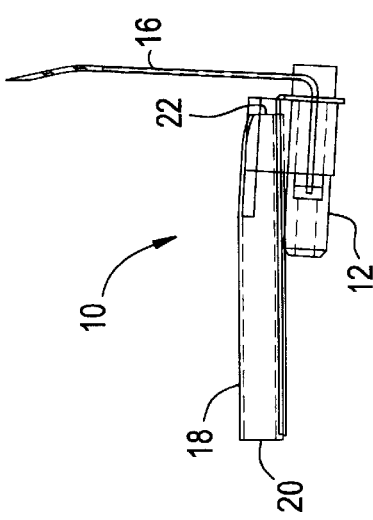
FIG. 3 is a side elevational view of the embodiment shown in FIG. 1.
Figure 10:
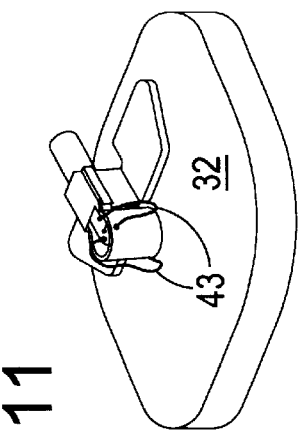
FIG. 10 is similar to FIG. 6 except that a second embodiment of the apparatus of the invention is shown.

While the invention will be described in connection with one or more preferred embodiments, it will be understood that the description is not intended to limit the invention to the described embodiments. On the contrary, the description is intended to cover all alternatives, modifications and equivalents as may be included within the spirit and scope of the invention as defined by the appended claims.

Turning now to the drawings in general and FIGS. 1-5 in particular, a first embodiment of a combination Huber needle assembly and needle safety guard 10 is shown. The needle assembly includes a main body 12, a pair of butterfly wings 14 extending outwardly from the main body 12 and a needle 16 extended substantially perpendicular from one end portion of main body 12.

The needle guard portion includes an elongated substantially hollow shield 18 which has open ends 20, 22 and an elongated slot 24 extending between the open ends 20, 22. A spring 26 connects between the main body 12 and the hollow shield 18. The spring 26 serves as a mechanism to pivot shield 18 with respect to main body 12 and needle 16.

As shown in FIG. 6, assembly 10 also includes a latch mechanism 28 in the form of a pair of curved arms extending from, in this case, shield 18 and around an end portion of main body 12. This causes shield 18 to be in a position substantially parallel to main body 12 and recessed in a groove 30 formed in a space between butterfly wings 14. This positioning of shield 18 in groove 30 allows maximum contact of the undersurface (not numbered) of wings 14 against the patients skin surface 32. FIG. 6 shows the apparatus of the invention in a position just prior to insertion of needle 16 into a subcutaneously located valve 34. The apparatus 10 is moved in the direction of arrow A for needle 16 to be inserted into an opening in valve 34. The position subsequent to insertion is shown in FIG. 7.

In FIG. 8, assembly 10 has been partially withdrawn from the patient's skin surface 32 in the direction of the arrow B. At this point, shield 18 has been unhooked or unlatched from latch 28 as shown in FIG. 6 and by virtue of spring force has partially pivoted toward needle 16 along the direction of arrow C. Pivot action of shield 18 has been partially inhibited by virtue of the distal end portion of shield 18 contacting the patient's skin surface 32. Further withdrawal of the apparatus 10 from the patient in the direction of arrow B causes the arrow to completely disengage from the patient's skin surface 32 as shown in FIG. 9 and has permitted shield 18 to complete its pivoting action in the direction of the arrow C such that needle 16 has moved through slot 24 and into the interior hollow portion of shield 18. In this manner, the distal most "sharp" portion of needle 16 is completely shielded such that the patient and/or healthcare provider will not be exposed to the sharp needle tip.

Thus, usage of the first embodiment apparatus of the invention can be employed in accordance with the following basic guidelines:
1. Remove the needle assembly from the sealed blister tray, separating the polyethylene (PE) tubing guard from the needle.
2. Fully insert the needle into the port/valve. Administer treatment as necessary.
3. Press the circular safety clamp to release the needle safety guard, which springs toward the surface of the port/valve. By squeezing together the butterfly wings and pulling the assembly upward, carefully remove the needle from the port/valve.
4. Upon full extraction, the safety guard encapsulates the needle. The design of the guard opening allows for easy entry of the needle when being captured, but restricts it from exiting the guard.

Referring now to FIGS. 10-13 and a second embodiment of the invention, an assembly 10 is shown just prior to positioning an insertion of a needle 16 into a valve 34 subcutaneously located with respect to the patient's skin surface 32. In this embodiment, a different shield mechanism is employed, although the basic construction of main body 12, butterfly wings 14 and needle 16 is substantially the same as in the first embodiment.

However, a shield 36 in the shown embodiment is collar-shaped. The shield 36 has a latch mechanism 38 in the form of a pair of arms extending outwardly therefrom and which are capable of engaging a pair of elongated outwardly extending ribs 40 on the main body 12. This structure is especially well shown in FIGS. 12 and 13.

Figure 11:
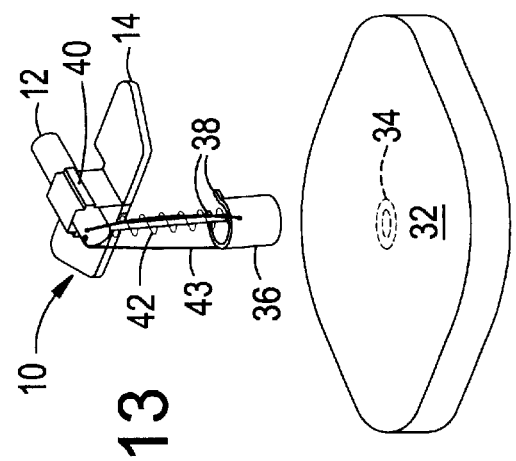
FIG. 11 is similar to FIG. 7 except that a second embodiment shown in FIG. 10 is utilized.
Figure 12:
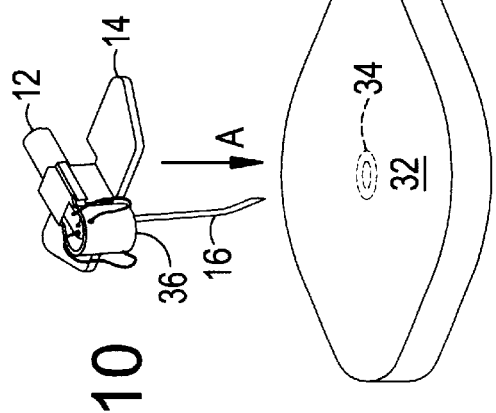
FIG. 12 is similar to FIG. 8 except that the second embodiment of the apparatus is employed.

FIG. 11 shows the assembly having been inserted into valve 34 (not shown) subcutaneously located with respect to the patient's skin surface 32. In FIG. 12, the assembly 10 has been partially withdrawn as shown by the arrow B such that needle 16 has been partially withdrawn from the patient's skin surface 32. At this point, latch 38 has been disengaged from ribs 40 such that spring force supplied by coiled spring 42, which surrounds needle 16 and extends from main body 12 and connects to shield 36 causes the shield to remain against the patient's skin surface 32.

Figure 13:
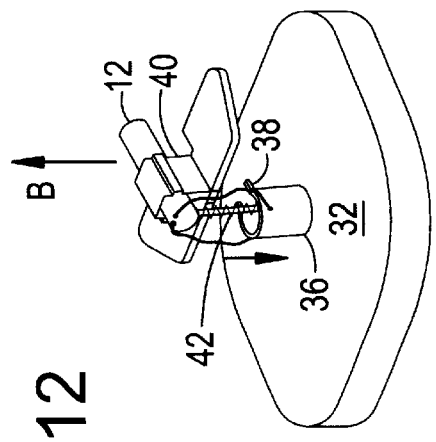
FIG. 13 is similar to FIG. 9 except that the second embodiment of the invention is employed.

As shown in FIG. 13, needle 16 has been completely withdrawn from the patient's skin surface and shield 36 has through spring force, slid further along needle 16 into a terminal position at the distal end of needle 16 such that the patient and healthcare provider are completely protected from the sharp needle distal tip. It is especially preferred to have tethers 43 which do not permit further spring force to allow shield 36 to extend beyond the distal tip of needle 16.

Usage of the second embodiment is briefly described as follows:
1. Remove the needle assembly from the sealed blister tray, separating the PE tubing guard from the needle. Position the exposed needle perpendicular to the port/valve surface. NOTE: Initial position of cylindrical guard/shield is secured to needle hub and does not restrict access of the needle to the port/valve.
2. Fully insert the needle into the port/valve. Administer treatment as necessary.
3. Release the cylindrical guard from the butterfly wings, squeeze together the butterfly wings and to pull the needle out of the port. The tethered spring forces the cylindrical guard down the shaft of the needle and remains in contact with the port until assembly is completely removed.
4. The assembly is now completely removed and the cylindrical guard now encapsulates the needle tip. The tethered sheath on the spring restricts it from extending too far. The location of the thru-hole on the bottom surface of the cylindrical guard makes it extremely difficult to re-expose the sharp.

Turning to FIGS. 14-17, a third embodiment of the invention is shown. The third embodiment also has a main body 12. However, the main body has a pair of finger grips 44 to facilitate holding the apparatus in the appropriate manner and at the appropriate time. Connected to the main body 12 is a pair of foldable legs 46. In this case, each leg 46 has an upper portion 48 and lower portion 50 with a hinge connected therebetween. The hinge can simply be a score in the material forming the legs if desired.

The legs also connect to a cylindrical shield 54, which in turn connects to a substantially flat plate 56 that is essentially a substitute for butterfly wings 14 of the first and second embodiment of the invention. A latch mechanism in the form of a pair of arms 58 forming a clamp extends upwardly from the lower most portion of the lower legs 50. The arms 58 are sized and shaped to surround a portion of main body 12.

Operation of the third embodiment is shown sequentially in FIGS. 14-17. As in the case of the first and second embodiments, the third embodiment is employed such that needle 16 is moved in the direction of arrow A towards patient's skin surface 32 and subcutaneous valve 34. This is shown in FIG. 14. FIG. 15 shows the third embodiment of the apparatus fully in place and in contact with the patient's skin surface 32. At that point, the legs 46 remain in their folded position.

FIG. 16 shows the apparatus partially withdrawn from the patient's skin surface in the direction C. At that point, arms 58 have been detached from main body 12, thereby permitting legs 46 to partially unfold as plate 56 is retained in place and in contact with the patient's skin surface 32.

FIG. 17 shows the third embodiment of the assembly completely removed from the patient's skin surface 32 and legs 46 in their completely unfolded position, thereby causing shield 54 to slide along the length of needle 16 and into position to protect the patient and healthcare provider from the sharp distal portion of the needle 16.

The fundamental operation of the third embodiment is briefly described as follows:
1. Remove the needle assembly from the sealed blister tray, separating PE tubing guard from the needle. Position the exposed needle perpendicular to the port/valve surface.
2. Fully insert the needle into the port/valve. Administer treatment as necessary.

3. With one hand, slip index finger and middle finger onto the butterfly wings, stabilizing the butterfly wings and the patient surface. Using the other hand and with a twisting motion, unlock arms 58 that form the clamp securing the butterfly wings to the needle hub. While still holding down the butterfly wings, grab the needle hub and begin to pull the needle out of the port. Continue pulling the needle out of the port until the legs are fully extended.

4. The needle tip is now completely removed and the cylindrical guard in the butterfly design now encapsulates the needle tip. The legs connected to the needle hub as well as the butterfly restricts the guard from extending too far. The location of the thru-hold on the cylindrical guard's bottom surface makes it extremely difficult to re-expose the sharp.

The invention may be embodied in other specific forms without departing from the spirit or essential attributes thereof and, accordingly, reference should be made to the appended claims, in addition to the foregoing specification, as indicating the scope of the invention.

What is claimed is:

1. A combination needle assembly and needle safety guard comprising:
   a main body;
   a needle extending at an angle from an end portion of the main body;
   a shield having opposed open ends and having a hollow portion slidably positioned around the needle;
   a pair of folding legs connected between the main body and the shield; and,
   a fastener adapted to position the shield in a first position to maximize the needle exposure, and to permit the shield to slide along the needle to a second position through unfolding of the legs to surround and/or trap a distal end portion of the needle.

* * * * *